United States Patent
Balko et al.

(10) Patent No.: US 7,432,227 B2
(45) Date of Patent: Oct. 7, 2008

(54) 6-ALKYL OR ALKENYL-4-AMINOPICOLINATES AND THEIR USE AS HERBICIDES

(75) Inventors: Terry William Balko, Greenfield, IN (US); Ann Marie Buysse, Carmel, IN (US); Stephen Craig Fields, Indianapolis, IN (US); Nicholas Martin Irvine, Westfield, IN (US); William Chi-Leung Lo, Fishers, IN (US); Christian Thomas Lowe, Westfield, IN (US); John Sanders Richburg, Greenville, MS (US); Paul Richard Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 117 days.

(21) Appl. No.: 10/816,611

(22) Filed: Apr. 2, 2004

(65) Prior Publication Data

US 2004/0198608 A1    Oct. 7, 2004

Related U.S. Application Data

(60) Provisional application No. 60/459,892, filed on Apr. 2, 2003.

(51) Int. Cl.
*A01N 43/40* (2006.01)
*C07D 213/79* (2006.01)

(52) U.S. Cl. .................. 504/260; 504/244; 504/255; 546/296; 546/297; 546/311; 546/312

(58) Field of Classification Search .......... 504/244, 504/251, 252, 254, 255, 260; 546/250, 268.4, 546/268.1, 255, 280.4, 281.7, 283.4, 312, 546/306, 311, 297, 296
See application file for complete search history.

(56) References Cited

U.S. PATENT DOCUMENTS

| | | | | |
|---|---|---|---|---|
| 3,234,229 A | | 2/1966 | Redemann | 260/296 |
| 3,285,925 A | | 11/1966 | Johnston et al. | 260/294.9 |
| 3,317,549 A | | 5/1967 | Johnston | 260/294.9 |
| 3,325,272 A | | 6/1967 | Hamaker et al. | 71/2.5 |
| 3,334,108 A | | 8/1967 | Johnston | 260/294.8 |
| 3,755,338 A | | 8/1973 | Gulbenk | 260/295 |
| 3,953,461 A | * | 4/1976 | Denzel et al. | 546/114 |
| 3,965,108 A | * | 6/1976 | Denzel et al. | 546/114 |
| 3,971,800 A | * | 7/1976 | Denzel et al. | 546/117 |
| 3,971,801 A | * | 7/1976 | Denzel et al. | 546/117 |
| 4,003,908 A | * | 1/1977 | Denzel et al. | 546/118 |
| 4,022,779 A | * | 5/1977 | Denzel et al. | 544/350 |
| 4,077,955 A | * | 3/1978 | Denzel et al. | 544/350 |
| 4,091,219 A | * | 5/1978 | Denzel et al. | 544/117 |
| 5,783,522 A | | 7/1998 | Schaefer et al. | 504/294 |
| 5,958,837 A | | 9/1999 | Schaefer et al. | 504/244 |
| 6,077,650 A | | 6/2000 | Price | 430/461 |
| 6,297,197 B1 | * | 10/2001 | Fields et al. | 504/260 |
| 6,352,635 B2 | * | 3/2002 | Krumel et al. | 205/426 |
| 6,784,137 B2 | * | 8/2004 | Balko et al. | 504/244 |
| 7,199,119 B2 | * | 4/2007 | Burkitt et al. | 514/233.8 |
| 7,291,580 B2 | * | 11/2007 | Balko et al. | 504/244 |

FOREIGN PATENT DOCUMENTS

| | | |
|---|---|---|
| BE | 788756 | 3/1973 |
| EP | 972765 | 1/2000 |
| WO | 98/21199 | 5/1998 |
| WO | 01/51684 | 7/2001 |
| WO | 03/011853 | 2/2003 |

OTHER PUBLICATIONS

Ramanand, et al, Reductive Dechlorination of the Nitrogen Hetercycli Herbicide Picloram, *Applied and Environmental Microbiology*, vol. 59, No. 7, Jul. 1993; pp. 2251-2256.

* cited by examiner

*Primary Examiner*—Sabiha N. Qazi
(74) *Attorney, Agent, or Firm*—Craig Mixan

(57) ABSTRACT

4-Aminopicolinic acids having alkyl or alkenyl substituents in the 6-position and their amine and acid derivatives are potent herbicides demonstrating a broad spectrum of weed control.

5 Claims, No Drawings

6-ALKYL OR ALKENYL-4-AMINOPICOLINATES AND THEIR USE AS HERBICIDES

CROSS-REFERENCE TO RELATED APPLICATIONS

The present application claims the benefit of U.S. Provisional Application Ser. No. 60/459,892 filed on Apr. 2, 2003.

BACKGROUND OF THE INVENTION

This invention relates to certain novel 6-alkyl or alkenyl-4-aminopicolinates and their derivatives and to the use of these compounds as herbicides.

A number of picolinic acids and their pesticidal properties have been described in the art. For example, U.S. Pat. No. 3,285,925 discloses 4-amino-3,5,6-trichloropicolinic acid derivatives and their use as plant growth control agents and herbicides. U.S. Pat. No. 3,325,272 discloses 4-amino-3,5-dichloropicolinic acid derivatives and their use for the control of plant growth. U.S. Pat. No. 3,317,549 discloses 3,6-dichloropicolinic acid derivatives and their use as plant growth control agents. U.S. Pat. No. 3,334,108 discloses chlorinated dithiopicolinic acid derivatives and their use as parasiticides. U.S. Pat. No. 3,234,229 discloses 4-amino-polychloro-2-trichloromethylpyridines and their use as herbicides. U.S. Pat. No. 3,755,338 discloses 4-amino-3,5-dichloro-6-bromopicolinates as fungicides. Belgian patent 788 756 discloses 6-alkyl-4-amino-3,5-dihalopicolinic acids as herbicides In Applied and Environmental Microbiology, Vol. 59, No. 7, July 1993, pp. 2251-2256, 4-amino-3,6-dichloropicolinic acid is identified as a product of the anaerobic degradation of 4-amino-3,5,6-trichloropicolinic acid, the commercially available herbicide picloram. U.S. Pat. No. 6,297,197 B1 describes certain 4-aminopicolinates and their use as herbicides. U.S. Pat. No. 5,783,522 discloses certain 6-phenyl picolinic acids and their use as herbicides, desiccants and defoliating agents. WO 0311853 describes certain 6-aryl-4-aminopicolinates and their use as herbicides. WO 9821199 discloses 6-pyrazolylpyridines and their use as herbicides. U.S. Pat. No. 5,958,837 discloses the synthesis of 6-arylpicolinic acids and their use as herbicides, desiccants and defoliating agents. U.S. Pat. No. 6,077,650 discloses the use of 6-phenylpicolinic acids as photographic bleaching agents, and European Patent EP 0 972 765 A1 discloses the synthesis of 2-, 3- or 4-arylpyridines.

SUMMARY OF THE INVENTION

It has now been found that certain 6-alkyl or alkenyl-4-aminopicolinic acids and their derivatives are potent herbicides with a broad spectrum of weed control against woody plants, grasses and sedges as well as broadleafs and with excellent crop selectivity. The compounds further possess excellent toxicological or environmental profiles.

The invention includes compounds of Formula I:

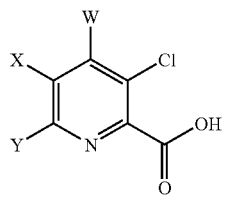

I wherein
X represents H or F;
Y represents $C_1$-$C_4$ alkyl, $C_1$-$C_4$ alkoxy substituted $C_1$-$C_4$ alkyl, $C_1$-$C_4$ thioalkoxy substituted $C_1$-$C_4$ alkyl, or $C_2$-$C_3$ alkenyl; and
W represents —$NO_2$, —$N_3$, —$NR_1R_2$, —N=$CR_3R_4$ or —NHN=$CR_3R_4$ wherein
$R_1$ and $R_2$ independently represent H, $C_1$-$C_6$ alkyl, $C_3$-$C_6$ alkenyl, $C_3$-$C_6$ alkynyl, aryl, heteroaryl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated or unsaturated ring which may contain additional O, S or N heteroatoms; and
$R_3$ and $R_4$ independently represent H, $C_1$-$C_6$ alkyl, $C_3$-$C_6$ alkenyl, $C_3$-$C_6$ alkynyl, aryl or heteroaryl or $R_3$ and $R_4$ taken together with =C represent a 5- or 6-membered saturated ring; and
agriculturally acceptable derivatives of the carboxylic acid group or the 4-amino group.

Compounds of Formula I wherein X represents F, wherein Y represents $CH_3$ or $CH_2CH_3$, and wherein W represents $NR_1R_2$ and $R_1$ and $R_2$ represent H or $C_1$-$C_6$ alkyl, are independently preferred.

The invention includes herbicidal compositions comprising a herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 4-aminopicolinic acids of Formula II:

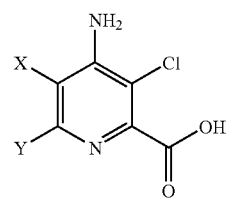

II

These compounds are characterized by possessing Cl in the 3-position; by possessing hydrogen or fluorine in the 5-position; and by possessing $C_1$-$C_4$ alkyl, $C_1$-$C_4$ alkoxy substituted $C_1$-$C_4$ alkyl, $C_1$-$C_4$ thioalkoxy substituted $C_1$-$C_4$ alkyl, or $C_2$-$C_3$ alkenyl substituents in the 6-position with methyl and ethyl being preferred.

The amino group at the 4-position can be unsubstituted or substituted with one or more $C_1$-$C_6$ alkyl, $C_3$-$C_6$ alkenyl, $C_3$-$C_6$ alkynyl, aryl, heteroaryl, hydroxy, $C_1$-$C_6$ alkoxy or amino substituents. The amino group can be further derivatized as an amide, a carbamate, a urea, a sulfonamide, a silylamine, a phosphoramidate, an imine or a hydrazone. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the picolinic acid is derivatized to form a related substituent that can be transformed within plants or the environment to the acid group possess essentially the same herbicidal effect and are within the scope of the invention. Therefore, an "agriculturally acceptable derivative", when used to describe the carboxylic acid functionality at the 2-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 6-alkyl or alkenyl-4-aminopicolinic acid, and (b) is or can be hydrolyzed, oxidized or metabolized in plants or soil to the picolinic acid of Formula I that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 4-position, is defined as any salt, silylamine, phosphorylaminei, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 6-alkyl or alkenyl-4-aminopicolinic acid, and (b) is or can be hydrolyzed in plants or soil to a free amine of Formula II. N-Oxides which are also capable of breaking into the parent pyridine of Formula II are also covered by the scope of this invention.

Suitable salts include those derived from alkali or alkaline earth metals and those derived from ammonia and amines. Preferred cations include sodium, potassium, magnesium, and aminium cations of the formula:

$R_5R_6R_7NH^+$ wherein $R_5$, $R_6$, and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl", as well as derivative terms such as "aryloxy", refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The following heteroaryl groups are preferred:

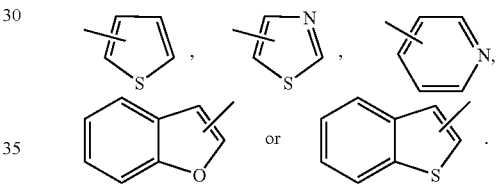

The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$OC(O)alkyl, $C_1$-$C_6$ NHC(O)alkyl, C(O)OH, $C_1$-$C_6$ C(O)Oalkyl, C(O)NH$_2$, $C_1$-$C_6$ C(O)NHalkyl, $C_1$-$C_6$ C(O)N(alkyl)$_2$, —OCH$_2$CH$_2$—, —OCH$_2$CH$_2$CH$_2$—, —OCH$_2$O— or —OCH$_2$CH$_2$O— provided that the substituents are sterically compatible and the rules of chemical bonding and strain energy are satisfied. Preferred substituents include halogen, $C_1$-$C_2$ alkyl and $C_1$-$C_2$ haloalkyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily synthesized utilizing standard procedures.

The 6-substituted alkyl or alkenylpyridines of Formula I can be prepared from a number of ways, which are well known in the art, e.g., by reaction of an appropriately substituted pyridine with a facile leaving group in the 6-position (III) with an organometallic compound of the type (IV) in an inert solvent in the presence of a transition metal catalyst.

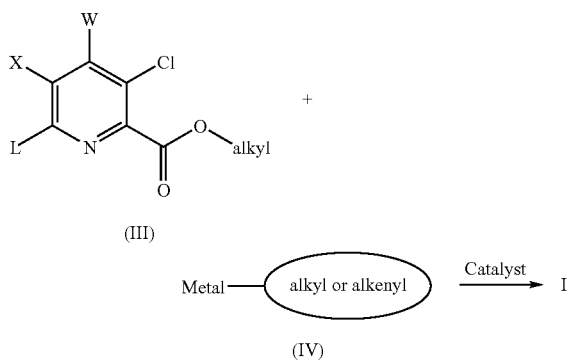

(III)

(IV)

In this case "L" can be chloro, bromo, iodo or trifluoromethanesulfonate, "Metal" can be Mg-halide, Zn-halide, tri-($C_1$-$C_4$ alkyl)tin, lithium, copper, or B(OR$^8$)(OR$^9$), where $R^8$ and $R^9$ are independently of one another, hydrogen, $C_1$-$C_4$ alkyl, or when taken together form an ethylene or propylene group, and "Catalyst" is a transition metal catalyst, in particular a palladium catalyst such as palladium diacetate or bis(triphenylphosphine)palladium(II)dichloride, or a nickel catalyst such as nickel(II)acetylacetonate or bis(triphenylphosphine)nickel(II) chloride.

Alternatively, compounds of Formula I can be prepared by reaction of an appropriately substituted 6-metal substituted pyridine (V) with an alkyl or alkenyl compound of the type (VI) in an inert solvent in the presence of a transition metal catalyst.

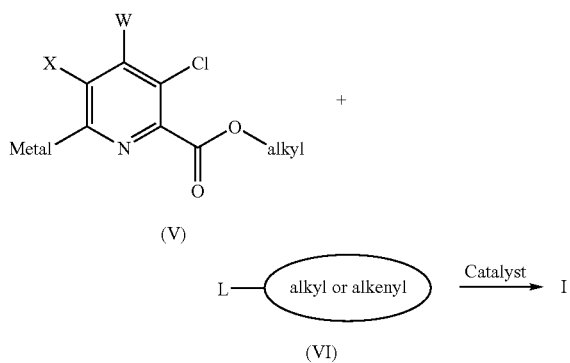

(V)

(VI)

In this case "L" can be chloro, bromo, iodo or trifluoromethanesulfonate and "Metal" can be Mg-halide, Zn-halide, tri-($C_1$-$C_4$ alkyl)tin, lithium, copper, or B(OR$^8$)(OR$^9$), where $R^8$ and $R^9$ are independently of one another, hydrogen, $C_1$-$C_4$ alkyl, or when taken together form an ethylene or propylene group, and "Catalyst" can be a transition metal catalyst, in particular a palladium catalyst such as palladium diacetate or bis(triphenylphosphine)palladium(II)dichloride, or a nickel catalyst such as nickel(II)acetylacetonate or bis(triphenylphosphine)nickel(II) chloride.

Reactions with boronic acids or esters are well known as exemplified by the following references:
(1) H-R. Ma et al., Synthetic Communications, 29(14), 2477 (1999);
(2) M. Gray et al., Tetrahedron Letters, 41(32), 6237 (2000).
(3) M H. Norman et al., Journal of Medicinal Chemistry, 43(22), 4288 (2000);
(4) Li, Jun et al., Current Medicinal Chemistry, 8(2), 121 (2001);

Reactions with Grignard compounds (metal=Mg-Hal):
(5) D. I. Davies et al., J. Chem. Soc. C, (15), 2019 (1969);
(6) Ohta et al., Heterocycles, 30(2, Spec. Issue), 875 (1990);
(7) M. Abarbri et al., Journal of Organic Chemistry, 65(15), 4618 (2000);
Reaction with organozinc compounds (metal=Zn-Hal):
(8) F. Trecourt et al., Journal of Organic Chemistry, 63(9), 2892 (1998);
(9) S. Khatib et al., Tetrahedron, 56(36), 6753 (2000);
(10) C. Rocaboy et al., Journal of Organic Chemistry, 67(20), 6863 (2002);
Reactions with organotin compounds (metal=Sn($C_1$-$C_4$ alkyl)$_3$):
(11) V. Colandrea et al., Tetrahedron Letters, 41(42), 8053 (2000);
(12) J. Li et al., Tetrahedron, 54(3/4), 393 (1998);
(13) E. Laborde et al., Journal of Heterocyclic Chemistry, 28(1), 191 (1991);

The coupling of III+IV, or V+VI may, where appropriate, be followed by reactions on the pyridine ring to obtain further derivatives of the compounds of Formula I.

Appropriate reactions such as displacement of the corresponding 4-halopyridines with NaN$_3$, followed by reduction of the corresponding 4-azido derivatives provide an amino group at the 4-position. Carbonylation under standard conditions provides the carboxylic acid at the 2-position.

Appropriately substituted pyridines of Formula III where L is chloro, bromo, iodo or trifluoromethanesulfonate can be easily obtain by well-known methods; see WO 0151468. For example, 6-bromo analogs can be prepared by the reduction of several key intermediates, e.g., the corresponding 6-bromo-4-azido, 6-bromo-4-nitro, and 6-bromo-4-nitro pyridine N-oxide analogs. These intermediates, in turn, can be prepared either by nucleophilic displacement of 6-bromo-4-halo analogs with NaN$_3$ or by electrophilic nitration of the corresponding 6-bromopyridine-N-oxides. Alternatively, such analogs can be prepared by direct amination of the corresponding 4,6-dibromo analogs.

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate. The imine or hydrazone can be prepared by reaction of the free amine or hydrazine with a suitable aldehyde or ketone.

Substituted 4-amino analogs can be prepared by reacting the corresponding 4-halopyridine-2-carboxylate or any other displaceable 4-substituent with the substituted amine.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of ways, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds post-emergence. It is further usually preferred to use the compounds to control a wide spectrum of woody plants, broadleaf and grass weeds, and sedges. Use of the compounds to control undesirable vegetation in established crops is especially indicated. While each of the 6-alkyl or alkenyl-4-aminopicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 2,000 g/Ha are generally employed in postemergence operations; for preemergence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulammethyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, imazethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, 4-amino-3,6-dichloropyridine-2-carboxylic acid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil and metribuzin. The herbicidal compounds of the present invention can, further, be used in conjunction with glyphosate and glufosinate on glyphosate-tolerant or glufosinate-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as cloquintocet, furilazole, dichlormid, benoxacor, mefenpyr-ethyl, fenclorazole-ethyl, flurazole, daimuron, dimepiperate, thiobencarb, fenclorim and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 6-alkyl or alkenyl-4-aminopicolinate compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims. Many of the starting materials useful for the preparation of the compounds of the present invention, e.g., 4-amino-3,6-dichloropyridine-2-carboxylic acid and methyl 4-amino-6-bromo-3-chloropyridine-2-carboxylate, are described in U.S. Pat. No. 6,297,197 B1.

EXAMPLES

1. Preparation of Methyl 4-amino-3,6-dichloro-5-fluoropyridine-2-carboxylate A solution of 4-amino-3,6-dichloropyridine-2-carboxylic acid (1100 g, 5.31 mol), 1-chloromethyl-4-fluoro-1,4-diazoniabicyclo[2.2.2]octanebis(tetrafluoroborate) (2100 g, 5.93 mol) in water (6000 mL) was warmed to 65° C. for six hours. After cooling to ambient temperature, the reaction mixture was stirred an additional 18 hours. The solution was concentrated and the resulting solid washed with 6 N hydrochloric acid (5×1000 mL) and dried to give 4-amino-3,6-dichloro-5-fluoropyridine-2-carboxylic acid (757 g, 3.53 mol. 58% purity). This crude material was added to methanol (3000 mL) which had been saturated with anhydrous hydrogen chloride and the reaction mixture was warmed to 45° C. for 2 hours. The solution was added with vigorous stirring to ice water (4000 mL) and the resulting solid collected. The crude ester was dissolved in ethyl acetate (1000 mL) and washed with saturated sodium bicarbonate solution (2×1000 mL), dried, and concentrated. The resulting solid was recrystallized from ethyl acetate/hexanes to give methyl 4-amino-3,6-dichloro-5-fluoropyridine-2-carboxylate (402.5 g, 1.67 mol), mp 128-131° C.

2. Preparation of Methyl 4-amino-3-chloro-5-fluoro-6-vinylpyridine-2-carboxylate (Compound 1)

A solution of methyl 4-amino-3,6-dichloro-5-fluoropyridine-2-carboxylate (8.00 g, 33.0 mmol), tributyl(vinyl)tin (13.27 g, 42.0 mmol) and cesium fluoride (11.19 g, 73.6 mmol) in dimethylformamide (250 mL) was sparged with nitrogen for 15 minutes. Dichlorobis(triphenylphosphine) palladium (II) (1.17 g, 1.6 mmol) was then added and the mixture was heated at 90° C. overnight. After cooling, the mixture was concentrated, taken up into ethyl acetate and filtered through a silica gel plug. The solvents were removed and the crude product was purified by column chromatography (50% ethyl acetate in hexane) to give methyl 4-amino-3-chloro-5-fluoro-6-vinylpyridine-2-carboxylate (5.13 g, 22.2 mmol), mp 68-71° C.

The following pyridine-2-carboxylate was prepared according to the procedure of Example 2:
Methyl 4-amino-3-chloro-6-vinylpyridine-2-carboxylate, mp 75-76° C. (Compound 2)

3. Preparation of Methyl 4-amino-3-chloro-6-ethyl-5-fluoropyridine-2-carboxylate (Compound 3)

A solution of methyl 4-amino-3-chloro-5-fluoro-6-vinylpyridine-2-carboxylate (3.00 g, 13.0 mmol) and 10% Pd/C (0.30 g) in ethanol (200 mL) was stirred under an atmosphere of hydrogen at 20 psi using a Parr apparatus for 1 hour. The mixture was filtered through celite, concentrated and the residue purified by column chromatography (50% ethyl acetate in hexane) to provide methyl 4-amino-3-chloro-6-ethyl-5-fluoropyridine-2-carboxylate (2.35 g, 10.0 mmol), mp 109-110° C.

The following pyridine-2-carboxylate was prepared according to the procedure of Example 3:
Methyl 4-amino-3-chloro-6-ethylpyridine-2-carboxylate, mp 84-85° C. (Compound 4)

4. Preparation of 4-Amino-3-chloro-6-ethyl-5-fluoropyridine-2-carboxylic acid (Compound 5)

A solution of lithium hydroxide (0.49 g, 11.73 mmol) in water (25 mL) was added to a solution of methyl 4-amino-3-chloro-6-ethyl-5-fluoropyridine-2-carboxylate (1.36 g, 5.86 mmol) in tetrahydrofuran (25 mL). The mixture was vigorously stirred at room temperature overnight and was then concentrated to half volume. After adding water the reaction mixture was washed once with ethyl acetate to remove unreacted starting material. The aqueous layer was then acidified to pH<3 with 1N HCl, concentrated and the residue partitioned between tetrahydrofuran and brine. The aqueous layer was discarded and the organic layer concentrated and dried under vacuum to provide 4-amino-3-chloro-6-ethyl-5-fluoropyridine-2-carboxylic acid (1.01 g, 4.60 mmol) as a white solid, mp 144-145° C.

The following pyridine-2-carboxylic acids were prepared according to the procedure of Example 4:
4-Amino-3-chloro-6-ethylpyridine-2-carboxylic acid, mp 140-142° C. (Compound 6)
4-Amino-3-chloro-6-methyl-5-fluoropyridine-2-carboxylic acid, mp 136-139° C. (Compound 7)
4-Amino-3-chloro-6-methylpyridine-2-carboxylic acid, mp 205° C. dec. (Compound 8)
4-Amino-3-chloro-6-(methoxymethyl)pyridine-2-carboxylic acid, mp 175-178° C. (Compound 9)
4-Amino-3-chloro-6-[(methylthio)methyl]pyridine-2-carboxylic acid, mp 170-172° C. (Compound 10)
6-Allyl-4-amino-3-chloropyridine-2-carboxylic acid; $^1$H NMR (d$^6$DMSO): δ 7.33 (br.s, 2H), 6.63 (s, 1H), 5.92 (m, 1H), 5.15 (m, 1H), 3.40 (d, J=6.6 Hz, 2H). (Compound 11)

5. Preparation of Methyl 4-amino-3-chloro-5-fluoro-6-methylpyridine-2-carboxylate (Compound 12)

A solution of methylboronic acid (0.17 g, 2.93 mmol), cesium fluoride (0.95 g, 6.27 mmol), 1,4-bis(diphenylphosphino)butane (0.09 g, 0.21 mmol), methyl 4-amino-3,6-dichloro-5-fluoropyridine-2-carboxylate (0.50 g, 2.09 mmol) and triethylamine (1 mL) in acetonitrile (20 mL) was purged for 15 minutes with nitrogen. Palladium acetate (0.05 g, 0.21 mmol) was then added and the reaction mixture heated under reflux overnight. After cooling, water was added and the mixture extracted with ethyl acetate. The organic layer was washed with brine, dried (MgSO$_4$), and concentrated. The residue was purified by column chromatography (33% ethyl acetate in hexane) to give methyl 4-amino-3-chloro-5-fluoro-6-methylpyridine-2-carboxylate (0.23 g, 1.05 mmol), mp 113-114° C.

The following pyridine-2-carboxylate was prepared according to the procedure of Example 5:
Methyl 4-amino-3-chloro-6-methylpyridine-2-carboxylate, mp 125-127° C. (Compound 13)

6. Preparation of Di-tert-butyl chloro[5-chloro-6-(methoxycarbonyl)-1-oxidopyridin-2-yl]malonate Di-tert-butylmalonate (9.70 g, 45.0 mmol) was added dropwise to a suspension of sodium hydride (60% in oil, 3.90 g, 97.5 mmol) in anhydrous tetrahydrofuran (20 mL) and stirred until no more hydrogen was given off. A solution of methyl 3,6-dichloropyridine-2-carboxylate 1-oxide (10.00 g, 45.0 mmol) in a minimum amount of anhydrous tetrahydrofuran was then added slowly by addition funnel and the reaction mixture was stirred at reflux for 3 hours. After cooling to 0° C., sulfuryl chloride (5.43 mL, 67.5 mmol) was added slowly and the mixture was allowed to warm to room temperature over 1.5 hrs. The reaction mixture was then diluted with ethyl acetate and washed several times with saturated NaHCO$_3$ solution. The organic layer was dried (MgSO$_4$), filtered and concentrated to dryness to give di-tert-butyl chloro[5-chloro-6-(methoxycarbonyl)-1-oxidopyridin-2-yl]malonate (19.65 g, 45.0 mmol) as a yellow solid; $^1$H NMR (CDCl$_3$): δ 7.90 (d, 1H), 4.00 (s, 3H), 1.40 (s, 18H).

7. Preparation of Methyl 3-chloro-6-(chloromethyl)pyridine-2-carboxylate 1-oxide A mixture of di-tert-butyl chloro[5-chloro-6-(methoxycarbonyl)-1-oxidopyridin-2-yl]malonate (19.65 g, 45.0 mmol), trifluoroacetic acid (41 mL) and dichloromethane (82 mL) was refluxed for 2.5 hours, cooled and then concentrated to dryness. The crude residue was taken up in xylene and the mixture heated at reflux until carbon dioxide was no longer given off. The reaction mixture was then cooled to room temperature and ethyl ether added followed by a small amount of saturated NaHCO$_3$ solution. The organic was separated and the aqueous layer was saturated with brine and extracted with ethyl acetate. The organic layers were combined, dried (MgSO$_4$), filtered and concentrated to dryness. The crude product was purified by column chromatography (20-50% ethyl acetate in hexane) to give methyl 3-chloro-6-(chloromethyl)pyridine-2-carboxylate 1-oxide (7.11 g, 30.1 mmol) as a brown solid; $^1$H NMR (CDCl$_3$): δ 7.60 (d, 2H), 7.40 (d, 2H), 4.80 (s, 2H), 4.00 (s, 3H).

8. Preparation of Methyl 3-chloro-6-(methoxymethyl)pyridine-2-carboxylate 1-oxide A solution of methyl 3-chloro-6-(chloromethyl)pyridine-2-carboxylate 1-oxide (1.50 g, 6.35 mmol) in methanol (15 mL) was cooled to 0° C. A 25% solution of sodium methoxide in methanol (1.52 mL) was added and the mixture stirred at room temperature for 6 days. The reaction mixture was diluted with ethyl acetate and washed with water. To the aqueous layer was added brine solution and was extracted with ethyl acetate. The organic layers were combined, dried (MgSO$_4$), filtered and concentrated to dryness to give crude methyl 3-chloro-6-(methoxymethyl)pyridine-2-carboxylate 1-oxide (1.14 g, 4.92 mmol) as a yellow oil; $^1$H NMR (CDCl$_3$): δ 7.50 (d, 1H), 7.40 (d, 1H), 4.60 (s, 2H), 4.10 (s, 3H), 3.50 (s, 3H).

9. Preparation of Methyl 3-chloro-6-[(methylthio)methyl]pyridine-2-carboxylate 1-oxide A solution of methyl 3-chloro-6-(chloromethyl)pyridine-2-carboxylate 1-oxide (3.35 g, 14.19 mmol) in tetrahydrofuran (20 mL) was cooled to 0° C. Sodium thiomethoxide (1.04 g, 14.90 mmol) was then added and the mixture stirred at room temperature for 4 hours. The reaction mixture was diluted with ethyl acetate and washed with water. The aqueous layer was saturated with brine and extracted several times with ethyl acetate. The organic layers were combined, dried (MgSO$_4$), filtered and concentrated to dryness to give crude methyl 4-amino-3-chloro-6-[(methylthio)methyl]pyridine-2-carboxylate 1-oxide (3.80 g) as a brown solid; $^1$H NMR (CDCl$_3$): δ 7.50 (d, 1H), 7.30 (d, 1H), 4.00 (s, 3H), 3.90 (s, 2H), 2.20 (s, 3H).

10. Preparation of Methyl 3,4-dichloro-6-(methoxymethyl)pyridine-2-carboxylate To a solution of methyl 3-chloro-6-(methoxymethyl)pyridine-2-carboxylate 1-oxide (1.64 g, 7.08 mmol) in acetonitrile (28 mL) was added phosphorus oxychloride (1.32 mL, 14.16 mmol) and the mixture stirred at reflux for 4 hours. After cooling to room temperature the mixture was concentrated to dryness in vacuo. The residue was diluted with ethyl ether and carefully washed with saturated NaHCO$_3$ solution. The organic layer was separated and the aqueous layer was extracted with ethyl ether. After the organic layers were combined, the solution was dried (MgSO$_4$), filtered and concentrated to dryness to give crude methyl 3,4-dichloro-6-(methoxymethyl)pyridine-2-carboxylate (1.74 g) as a yellow oil; $^1$H NMR (CDCl$_3$): δ 7.70 (s, 1H), 4.60 (s, 2H), 4.00 (s, 3H), 3.40 (s, 3H).

The following pyridine-2-carboxylate was prepared according to the procedure of Example 10:
Methyl 3,4-dichloro-6-[(methylthio)methyl]pyridine-2-carboxylate; $^1$H NMR (CDCl$_3$): δ 7.70 (s, 1H), 4.00 (s, 3H), 3.90 (s, 2H), 2.10 (s, 3H).

11. Preparation of Methyl 4-amino-3-chloro-6-(methoxymethyl)pyridine-2-carboxylate (Compound 14)

Methyl 3,4-dichloro-6-(methoxymethyl)pyridine-2-carboxylate (1.74 g, 6.96 mmol) was dissolved in a minimum amount of dimethylformamide. Sodium azide (0.50 g, 7.65 mmol) was added carefully followed by a small volume of water to form a homogenous mixture. The reaction mixture was then stirred at 70° C. for 48 hours. The mixture was cooled and concentrated to near dryness to provide the crude azide. The crude product was immediately dissolved in a minimum amount of methanol and cooled in an ice bath. Sodium borohydride (0.11 g, 2.92 mmol) was carefully added and the mixture allowed to warm to room temperature over 15 minutes. The reaction mixture was then diluted with ethyl acetate and washed several times with water. The organic layer was dried ($MgSO_4$), filtered and concentrated to dryness. The crude product was purified by column chromatography (20-50% ethyl acetate in hexane) to give methyl 4-amino-3-chloro-6-(methoxymethyl)pyridine-2-carboxylate (0.35 g, 1.52 mmol) as a white solid; $^1$H NMR ($CDCl_3$): δ 6.90 (s, 1H), 4.80 (br.s, 2H), 4.50 (s, 2H), 4.00 (s, 3H), 3.40 (s, 3H).

The following pyridine-2-carboxylate was prepared according to the procedure of Example 11:

Methyl 4-amino-3-chloro-6-[(methylthio)methyl]pyridine-2-carboxylate; $^1$H NMR ($CDCl_3$): δ 6.90 (s, 1H), 4.00 (s, 3H), 3.70 (s, 2H), 2.10 (s, 3H). (Compound 15)

12. Preparation of Herbicidal Compositions

In the following illustrative compositions, parts and percentages are by weight.

Emulsifiable Concentrates

Formulation A

|  | WT % |
|---|---|
| Compound 1 | 26.2 |
| Polyglycol 26-3 | 5.2 |
| Nonionic emulsifier-(di-sec-butyl)-phenyl-poly(oxypropylene)block polymer with (oxyethylene). The polyoxyethelene content is about 12 moles. |  |
| Witconate P12-20 (Anionic emulsifier-calcium dodecylbenzene sulfonate-60 wt. % active) | 5.2 |
| Aromatic 100 (Xylene range aromatic solvent) | 63.4 |

Formulation B

|  | WT % |
|---|---|
| Compound 3 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

Formulation C

|  | WT % |
|---|---|
| Compound 4 | 13.2 |
| Stepon C-65 | 25.7 |
| Ethomeen T/25 | 7.7 |
| Ethomeen T/15 | 18.0 |
| Xylene range aromatic solvent | 35.4 |

Formulation D

|  | WT % |
|---|---|
| Compound 14 | 30.0 |
| Agrimer Al-10LC (emulsifier) | 3.0 |
| N-methyl-2-pyrrolidone | 67.0 |

Formulation E

|  | WT % |
|---|---|
| Compound 13 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

Formulation F

|  | WT % |
|---|---|
| Compound 5 | 26.0 |
| Polyglycol 26-3 | 2.0 |
| Polyfon H | 4.0 |
| Zeosyl 100 (Precipitated hydrated $SiO_2$) | 17.0 |
| Barden clay + inerts | 51.0 |

Formulation G

|  | WT % |
|---|---|
| Compound 11 | 62.4 |
| Polyfon H (sodium salt of lignin sulfonate) | 6.0 |
| Sellogen HR (sodium naphthalene sulfonate) | 4.0 |
| Zeosyl 100 | 27.6 |

Formulation H

|  | WT % |
|---|---|
| Compound 7 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

Formulation I

|  | WT % |
|---|---|
| Compound 6 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

Formulation J

|  | WT % |
|---|---|
| Compound 9 | 5.0 |
| Celetom MP-88 | 95.0 |

The active ingredient is applied in a polar solvent such as N-methyl-pyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

|  | WT % |
|---|---|
| Compound 11 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

Formulation L

|  | Wt % |
|---|---|
| Compound 5 | 3.67 |
| Monoethanolamine pH buffer | 0.5 |
| Water | 95.83 |

The active ingredient is dissolved in and appropiate amount of water and the additional monoethanolamine is added as a buffer. A water-soluble surfactant may be added. Other aids may be incorporated to improve physical, chemical and/or formulation properties.

13. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hr photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Tables 1-2. Selectivity to wheat and corn is shown in Tables 3 and 4.

TABLE 1

Post-emergent % control

| Compound | Rate (ppm) | XANST | CHEAL | ECHCG | SETFA |
|---|---|---|---|---|---|
| 1 | 250 | 100 | 100 | 60 | 50 |
| 3 | 250 | 100 | 100 | 85 | 80 |
| 5 | 250 | 100 | 100 | 85 | 70 |
| 7 | 288 | 100 | 98 | 80 | 85 |
| 12 | 250 | 100 | 100 | 80 | 95 |

XANST = Cocklebur (*Xanthium strumarium*)
CHEAL = Lambsquarter (*Chenopodium album*)
ECHCG = Barnyardgrass (*Echinochloa crus-galli*)
SETFA = Giant Foxtail (*Setaria faberi*)

TABLE 2

Post-emergent % control

| Compound | Rate (ppm) | XANST | CHEAL | ECHCG | SETFA |
|---|---|---|---|---|---|
| 2 | 250 | 80 | 85 | 0 | 10 |
| 4 | 250 | 95 | 100 | 0 | 0 |
| 6 | 250 | 98 | 90 | 0 | 0 |
| 8 | 250 | 70 | 40 | 0 | 0 |
| 9 | 250 | 80 | 80 | 0 | 0 |
| 10 | 250 | 85 | 70 | 0 | 20 |
| 11 | 250 | 85 | 70 | 0 | 0 |
| 13 | 254 | 40 | 70 | 0 | 0 |

XANST = Cocklebur ((*Xanthium strumarium*)
CHEAL = Lambsquarter (*Chenopodium album*)
ECHCG = Barnyardgrass (*Echinochloa crus-galli*)
SETFA = Giant Foxtail (*Setaria faberi*)

TABLE 3

Post-emergent % control

| Compound | Rate (ppm) | CHEAL | AMARE | TRZAS |
|---|---|---|---|---|
| 4 | 250 | 100 | 98 | 0 |
| 6 | 250 | 90 | 100 | 0 |
| 13 | 254 | 70 | 90 | 0 |

CHEAL = Lambsquarter (*Chenopodium album*)
AMARE = Pigweed (redroot) (*Amaranthus retroflexus*)
TRZAS = Wheat(var.Merica) (*Triticum aestivum*)

TABLE 4

Post-emergent % control

| Compound | Rate (ppm) | XANST | CHEAL | AMARE | ZEAMX |
|---|---|---|---|---|---|
| 4 | 250 | 95 | 100 | 98 | 0 |
| 6 | 250 | 98 | 90 | 100 | 0 |
| 9 | 250 | 80 | 80 | 90 | 0 |
| 13 | 254 | 70 | 75 | 90 | 0 |

XANST = Cocklebur (*Xanthium strumarium*)
CHEAL = Lambsquarter (*Chenopodium album*)
AMARE = Pigweed (redroot) (*Amaranthus retroflexus*)
ZEAMX = Corn (#14 3377) (*Zea mays*)

14. Evaluation of Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 2 mL aliquots of the stock solution with 15 mL of the mixture and lower concentrations were prepared by serial dilution of the stock solution. A 2.5 mL aliquot of each solution of known concentration was sprayed evenly onto the soil surface (113 sq. cm) of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture.

The treated pots and control pots were placed in a greenhouse maintained with an approximate 15 hr photoperiod and temperatures of about 23-29° C. during the day and 22-28° C. during the night. Nutrients and water were added on a regular basis and supplemental lighting was provided with overhead metal halide 1000-Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination.

Some of the compounds tested, application rates employed, plant species tested, and results are given in Table 5.

TABLE 5

Pre-emergent % control

| Compound | Rate (ppm) | CHEAL | IPOHE | DIGSA | SETFA |
|---|---|---|---|---|---|
| 1 | 280 | 100 | 100 | 95 | 90 |
| 2 | 560 | 100 | 60 | 0 | 0 |
| 3 | 140 | 100 | 100 | 100 | 100 |
| 4 | 280 | 98 | 100 | 0 | 0 |
| 5 | 140 | 100 | 100 | 90 | 90 |
| 6 | 280 | 90 | 100 | 15 | 0 |
| 7 | 295 | 98 | 98 | 85 | 85 |
| 8 | 280 | 100 | 85 | 20 | 10 |
| 9 | 560 | 90 | 50 | 10 | 10 |
| 10 | 560 | 0 | 0 | 0 | 0 |
| 11 | 560 | 40 | 80 | 0 | 0 |
| 12 | 140 | 100 | 100 | 100 | 98 |
| 13 | 573 | 100 | 90 | 0 | 0 |

CHEAL = Lambsquarter (*Chenopodium album*)
IPOHE = Ivyleaf Morningglory (*Ipomoea hederacea*)
DIGSA = Crabgrass(large) (*Digitaria sanguinalis*)
SETFA = Giant Foxtail (*Setaria faberi*)

What is claimed is:

1. A compound of the formula I

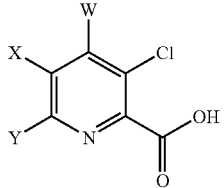

wherein
X represents F;
Y represents $C_1$-$C_4$ alkyl, $C_1$-$C_4$ alkoxy substituted $C_1$-$C_4$ alkyl, $C_1$-$C_4$ thioalkoxy substituted $C_1$-$C_4$ alkyl, or $C_2$-$C_3$ alkenyl; and
W represents —$NO_2$, —$N_3$, —$NR_1R_2$, —N=$CR_3R_4$ or —NHN=$CR_3R_4$
wherein
$R_1$ and $R_2$ independently represent H, $C_1$-$C_6$ alkyl, $C_3$-$C_6$ alkenyl, $C_3$-$C_6$ alkynyl, aryl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl; and
$R_3$ and $R_4$ independently represent H, $C_1$-$C_6$ alkyl, $C_3$-$C_6$ alkenyl, $C_3$-$C_6$ alkynyl or aryl; and
agriculturally acceptable derivatives of the carboxylic acid group or the 4-amino group.

2. The compounds of claim 1 in which Y represents $CH_3$ or $CH_2CH_3$.

3. The compounds of claim 1 in which W represents $NR_1R_2$ where $R_1$ and $R_2$ independently represent H or $C_1$-$C_6$ alkyl.

4. A herbicidal composition comprising a herbicidally effective amount of a compound of formula I

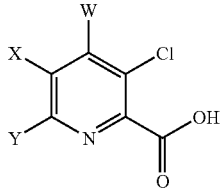

wherein
X represents F;
Y represents $C_1$-$C_4$ alkyl, $C_1$-$C_4$ alkoxy substituted $C_1$-$C_4$ alkyl, $C_1$-$C_4$ thioalkoxy substituted $C_1$-$C_4$ alkyl, or $C_2$-$C_3$ alkenyl; and
W represents —$NO_2$, —$N_3$, —$NR_1R_2$, —N=$CR_3R_4$ or —NHN=$CR_3R_4$
wherein
$R_1$ and $R_2$ independently represent H, $C_1$-$C_6$ alkyl, $C_3$-$C_6$ alkenyl,
$C_3$-$C_6$ alkynyl, aryl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl; and
$R_3$ and $R_4$ independently represent H, $C_1$-$C_6$ alkyl, $C_3$-$C_6$ alkenyl, $C_3$-$C_6$ alkynyl or aryl; and
agriculturally acceptable derivatives of the carboxylic acid group or the 4-amino group
in admixture with an agriculturally acceptable adjuvant or carrier.

5. A method of controlling undesirable vegetation which comprises contacting the vegetation or the locus thereof with or applying to the soil to prevent the emergence of vegetation an herbicidally effective amount of a compound of formula I

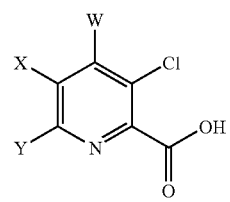

wherein
X represents F;
Y represents $C_1$-$C_4$ alkyl, $C_1$-$C_4$ alkoxy substituted $C_1$-$C_4$ alkyl, $C_1$-$C_4$ thioalkoxy substituted $C_1$-$C_4$ alkyl, or $C_2$-$C_3$ alkenyl; and
W represents —$NO_2$, —$N_3$, —$NR_1R_2$, —N=$CR_3R_4$ or —NHN=$CR_3R_4$
wherein
$R_1$ and $R_2$ independently represent H, $C_1$-$C_6$ alkyl, $C_3$-$C_6$ alkenyl, $C_3$-$C_6$ alkynyl, aryl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl; and
$R_3$ and $R_4$ independently represent H, $C_1$-$C_6$ alkyl, $C_3$-$C_6$ alkenyl, $C_3$-$C_6$ alkynyl or aryl; and
agriculturally acceptable derivatives of the carboxylic acid group or the 4-amino group.

* * * * *